(12) United States Patent
Evans

(10) Patent No.: US 9,402,536 B2
(45) Date of Patent: Aug. 2, 2016

(54) OBTURATOR FEATURES FOR MATING WITH CANNULA TUBE

(71) Applicant: Covidien LP, Mansfield, MA (US)

(72) Inventor: Christopher Kelly Evans, Meriden, CT (US)

(73) Assignee: Covidien LP, Mansfield, MA (US)

( * ) Notice: Subject to any disclaimer, the term of this patent is extended or adjusted under 35 U.S.C. 154(b) by 186 days.

(21) Appl. No.: 14/172,246

(22) Filed: Feb. 4, 2014

(65) Prior Publication Data

US 2014/0323808 A1    Oct. 30, 2014

Related U.S. Application Data

(60) Provisional application No. 61/817,402, filed on Apr. 30, 2013.

(51) Int. Cl.
| | | |
|---|---|---|
| *A61B 17/32* | (2006.01) | |
| *A61B 17/34* | (2006.01) | |
| *A61B 1/32* | (2006.01) | |
| *A61B 17/00* | (2006.01) | |

(52) U.S. Cl.
CPC .............. *A61B 1/32* (2013.01); *A61B 17/3417* (2013.01); *A61B 2017/00455* (2013.01); *A61B 2017/00477* (2013.01); *A61B 2017/3456* (2013.01)

(58) Field of Classification Search
CPC .................... A61B 17/3421; A61B 17/3417
See application file for complete search history.

(56) References Cited

U.S. PATENT DOCUMENTS

| | | | |
|---|---|---|---|
| 5,222,487 | A | 6/1993 | Carr et al. |
| 5,746,720 | A | 5/1998 | Stouder, Jr. |
| 8,298,185 | B2 | 10/2012 | Worrel et al. |
| 2009/0012362 | A1 | 1/2009 | Kucklick |
| 2009/0018394 | A1 | 1/2009 | Berberich et al. |
| 2010/0094228 | A1 | 4/2010 | Bettuchi et al. |
| 2010/0137895 | A1* | 6/2010 | Smith ............. A61B 17/32093 606/185 |
| 2011/0040149 | A1 | 2/2011 | Smith |

FOREIGN PATENT DOCUMENTS

WO     WO 2008/024883     2/2008

OTHER PUBLICATIONS

European Search Report dated Jun. 30, 2014 issued in European Application No. EP 14 16 6313.

* cited by examiner

*Primary Examiner* — David Bates

(57) ABSTRACT

A surgical assembly includes a cannula and an obturator. The cannula has open proximal and distal ends defining a lumen therebetween. The lumen defines an inner surface of the cannula having a mating structure. The obturator is generally tubular and has an outer surface including a corresponding mating structure. The respective mating structures of the obturator and the cannula engage each other so as prevent relative rotation of the obturator and cannula, and to prevent inadvertent disconnection of an upper valve housing attached to the cannula.

10 Claims, 10 Drawing Sheets

OBTURATOR FEATURES FOR MATING WITH CANNULA TUBE

CROSS-REFERENCE TO RELATED APPLICATIONS

This application claims the benefit of and priority to U.S. Provisional Patent Application No. 61/817,402, filed Apr. 30, 2013, the entire disclosure of which is incorporated by reference herein.

BACKGROUND

1. Technical Field

The present disclosure relates to an assembly for the penetration of body tissue. More particularly, the present disclosure relates to an obturator including features for engaging the inner surface of a cannula tube to apply torque directly to the cannula tube.

2. Background of Related Art

In endoscopic surgical procedures, surgery is performed in any hollow viscus of the body through a small incision or through narrow endoscopic tubes (cannulas) inserted through a small entrance wound in the skin or through a naturally occurring orifice. In laparoscopic procedures, surgery is performed in the interior of the abdomen. Laparoscopic and endoscopic procedures often require the clinician to act on organs, tissues and vessels far removed from the incision, thereby requiring that any instruments used in such procedures be of sufficient size and length to permit remote operation. Typically, after the surgical region is insufflated, a trocar is used to puncture the body cavity and includes a cannula which remains in place for use during the laparoscopic procedure. The cannula includes a housing which seals the opening created by the trocar and maintains the insufflation pressure within the body cavity. Generally, the housing is attached to the cannula by a twisting or bayonet connection. Medical devices can be inserted through the housing to access the underlying body cavity. The manipulation of the medical device, notably twisting or rotating, while the medical device is inserted through the housing can cause the housing to rotate or shift relative to the cannula. The rotation of the housing relative to the cannula can cause the housing to detach from the cannula or the seal between the cannula and the housing to be compromised. If the seal between the housing and the cannula is compromised or fails the insufflation pressure within the body cavity will be lost.

It may be advantageous to provide a surgical assembly including a medical device that can engage the inner surface of the cannula to maintain a fixed circumferential position with respect to the cannula and apply a twisting force directly to the cannula.

SUMMARY

Accordingly, the present disclosure relates to surgical assemblies for accessing body cavities during a surgical procedure.

The surgical assembly includes an obturator and a cannula. The obturator has an elongate tubular member with proximal portion and distal portions. The proximal portion may have an opening and the elongate tubular member may have a channel therein for optionally receiving an endoscope. The elongate tubular member includes an outer surface having a first mating structure. The obturator may include a distal tip portion beyond the end of the distal end of the elongate tubular member. The distal tip portion permitting viewing of a body cavity through the obturator.

The cannula includes a tubular body member having open proximal and distal ends. A lumen is defined between the open proximal and distal ends. The lumen defines an inner surface of the tubular body member and receives a portion of the elongate tubular member of the obturator. The inner surface includes a second mating structure which receives the first mating structure when the lumen receives the portion of the elongate tubular member of the obturator.

According to aspects of the disclosure, the tubular body member of the cannula includes a locking mechanism. The locking mechanism engages the outer surface of the elongate tubular member to lock the obturator within the lumen of the cannula. In some embodiments, the locking mechanism engages the first mating structure of the elongate tubular member. In certain embodiments, the locking mechanism engages a notch in the first mating structure. In particular embodiments, the locking mechanism forms a seal around the outer surface of the elongate tubular member.

In embodiments, the assembly also includes an upper seal housing. The upper seal housing engages a proximal portion of the cannula and has a sealing port disposed over the lumen. When the portion of the elongate tubular member of the obturator is received by the lumen, the portion of the elongate tubular member may pass through the sealing port. The sealing port may include a sealing member that forms a seal with the outer surface of the elongate tubular member.

According to some aspects of the disclosure, the first mating structure is disposed entirely within the second mating structure of the tubular body member of the cannula when the portion of the elongate tubular member of the obturator is received within the lumen of the cannula. In embodiments, the upper seal housing includes a third mating structure. In such embodiments, the third mating structure aligns with the second mating structure of the tubular body member when the upper seal housing engages the proximal portion of the cannula. In some embodiments, the third mating structure allows the first mating structure to pass through and be disposed entirely within the second mating structure of the tubular body member. In other embodiments, the third mating structure receives at least a portion of the first mating structure when the portion of the elongate tubular member of the obturator is received within the lumen of the cannula.

In embodiments, the first mating structure engages the second mating structure of the cannula to maintain a fixed circumferential position between the cannula and the obturator. In certain embodiments, the first mating structure engages the second mating structure of the cannula and the third mating structure in the sealing port to maintain a fixed circumferential position between the cannula, the upper seal housing, and the obturator.

In some embodiments, the obturator includes two or more first mating structures and the cannula includes two or more second mating structures. In such embodiments, each first mating structure may be received within a respective second mating structure. The two or more first mating structures may be circumferentially spaced equally or circumferentially spaced unequally on the elongate tubular member. In certain embodiments the cooperation of the first mating structure and the second mating structure defines a desired circumferential position of the obturator relative to the cannula. In particular embodiments the unequal circumferential spacing of the first mating structures defines the desired circumferential position. Equal spacing allows the obturator to be inserted in multiple relative orientations while unequal spacing would limit the number of insertion orientations.

According to aspects of the disclosure, a method for viewing a body cavity is disclosed. The method includes the steps of a method for accessing a body cavity, comprising: inserting an obturator within a lumen of a cannula, the obturator including an elongate tubular member having an outer surface, a first mating structure, and an open proximal end, the first mating structure received by a second mating structure of the tubular body member of the cannula, the cannula including a tubular body member having open proximal and distal ends defining a lumen therebetween, the lumen defining an inner surface of the tubular body member, the inner surface having the second mating structure, whereby inserting the obturator within the lumen of the cannula such that the first mating structure engages the second mating structure so as to prevent relative rotation of the obturator and the cannula;

creating an opening in a tissue layer using the obturator and the cannula. The method may include the step of securing a seal housing to a proximal portion of the cannula before the step of inserting the obturator. The method may also include the step of aligning a third mating structure within a sealing port of the upper seal housing with a second mating structure of the cannula.

An advantage of an obturator including mating structures that engage an inner surface of a cannula is that the cannula maintains a fixed circumferential position relative to the obturator thereby cooperating with the rotation of the obturator. Because the upper and lower parts of the assembly, the obturator and the cannula, rotate together, the assembly is more likely to maintain a seal with the body cavity, and thus, maintain the insufflation pressure within the body cavity. Maintaining the seal may also reduce the risk of infection to the body cavity. Further, when the assembly includes a locking mechanism that forms a seal around the outer surface of the obturator, the need for separate upper seal housing may be eliminated.

Another advantage of an obturator including mating structures that engage an inner surface of a cannula, is that a separate locking mechanism between the upper seal housing and the cannula to prevent inadvertent rotation of the upper seal housing relative to the cannula may be eliminated.

Still yet another advantage of an obturator including mating structures that engage an inner surface of a cannula, is that a reduction in the amount of rotation needed to connect the upper seal housing to the cannula may be reduced.

BRIEF DESCRIPTION OF THE DRAWINGS

The accompanying drawings, which are incorporated in and constitute a part of this specification, illustrate embodiments of the disclosure and, together with a general description of the disclosure given above, and the detailed description of the embodiment(s) given below, serve to explain the principles of the disclosure, wherein.

DETAILED DESCRIPTION OF THE DRAWINGS

As used herein, the term "distal" refers to the portion that is being described which is farther from a user, while the term "proximal" refers to the portion that is being described which is closer to a user. As used herein, the term "clinician" refers to an individual or group of individuals performing surgery on a patient including but not limited to a nurse, a doctor, or a surgeon. In the following description, well-known functions or constructions are not described in detail to avoid obscuring the present disclosure in unnecessary detail. Further, to the extent consistent, any of the aspects and embodiments described herein may be used in conjunction with any or all of the other aspects and embodiments described herein.

Figure 1:
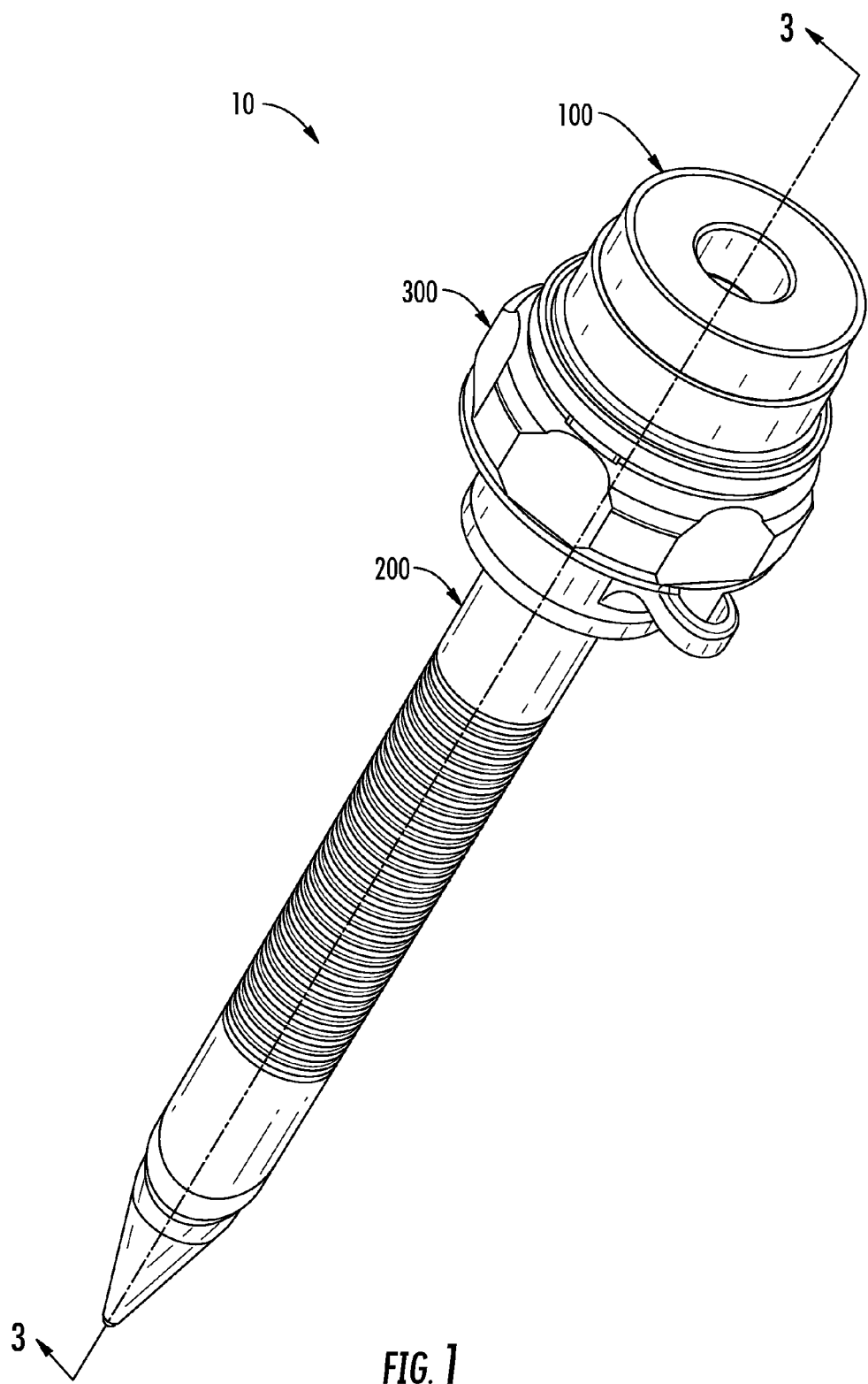
FIG. 1 is a perspective view of a surgical assembly in accordance with the principles of the present disclosure.
Figure 2:
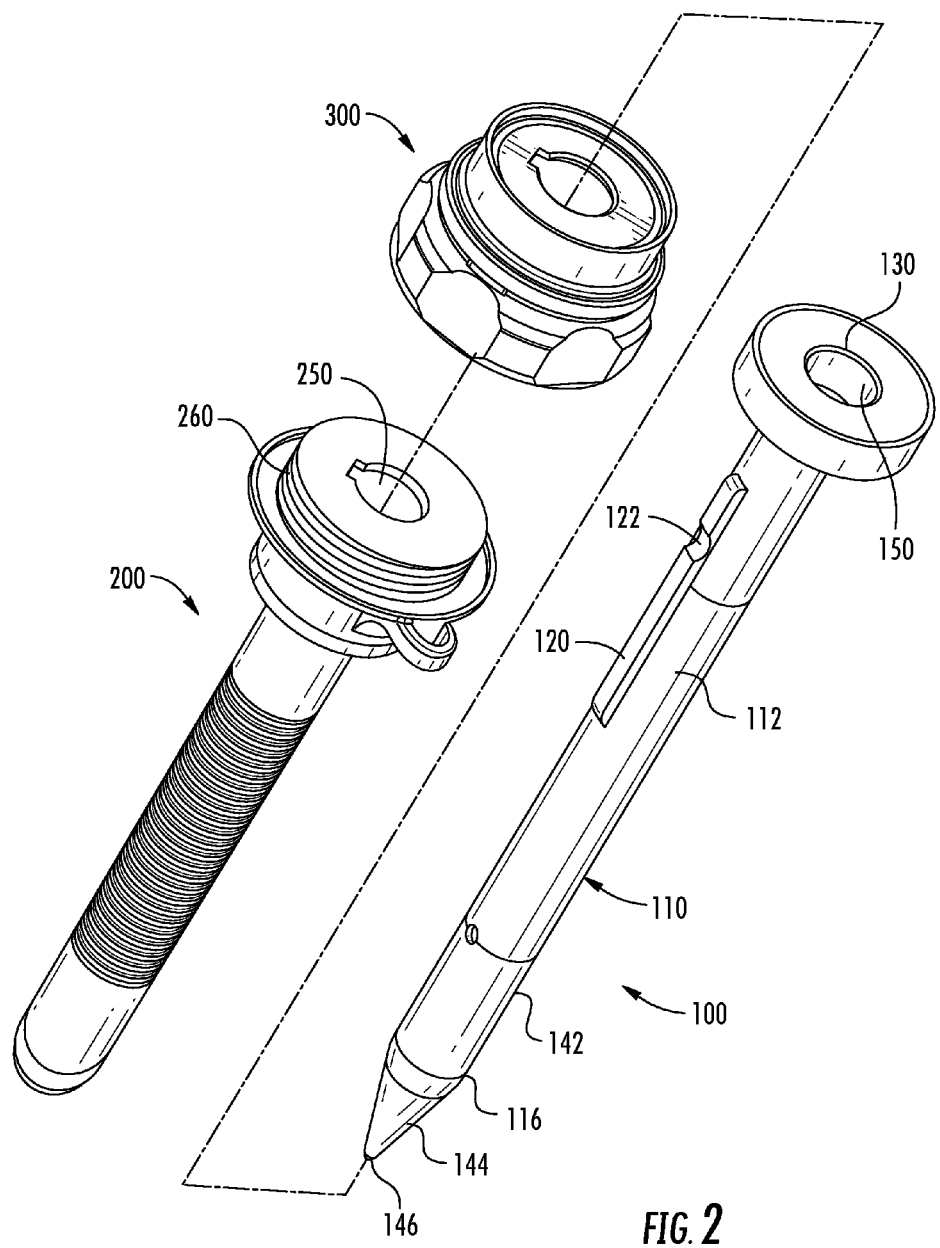
FIG. 2 is an exploded perspective view of the components of the surgical assembly of FIG. 1.
Figure 3:
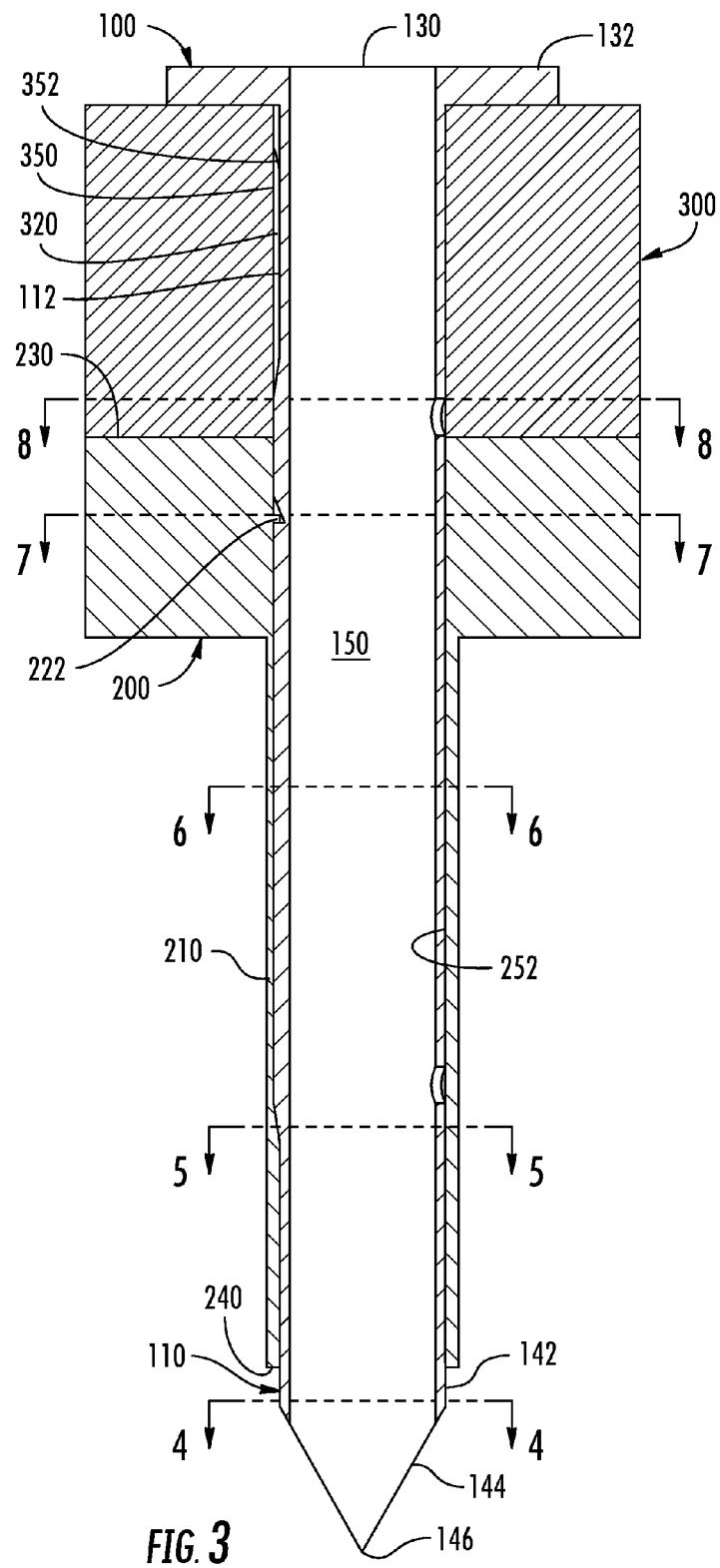
FIG. 3 is a side, cross-sectional view taken along the line 3-3 in FIG. 1.

Referring now to the drawings, in which like reference numerals identify identical or substantially similar parts throughout the several views, FIGS. 1 and 2 illustrate an exemplary embodiment of surgical assembly 10 which is in accordance with the present disclosure. Assembly 10 includes an obturator 100 and a cannula 200. Assembly 10 may also include an upper seal housing 300 secured to cannula 200 between obturator 100 and cannula 200. Obturator 100 has an elongate tubular member 110 including a proximal portion 130 and a distal portion 142. In embodiments, proximal end 130 is open and a channel 150 extends from proximal end 130 to distal portion 142 of elongate tubular member 110 as shown in FIG. 3. Channel 150 may receive an endoscope therein as shown FIG. 11. An outer surface 122 of elongate tubular member 110 includes a first mating structure 120. An elongate tubular member 110 including multiple first mating structures 120 is also contemplated.

Figure 10:
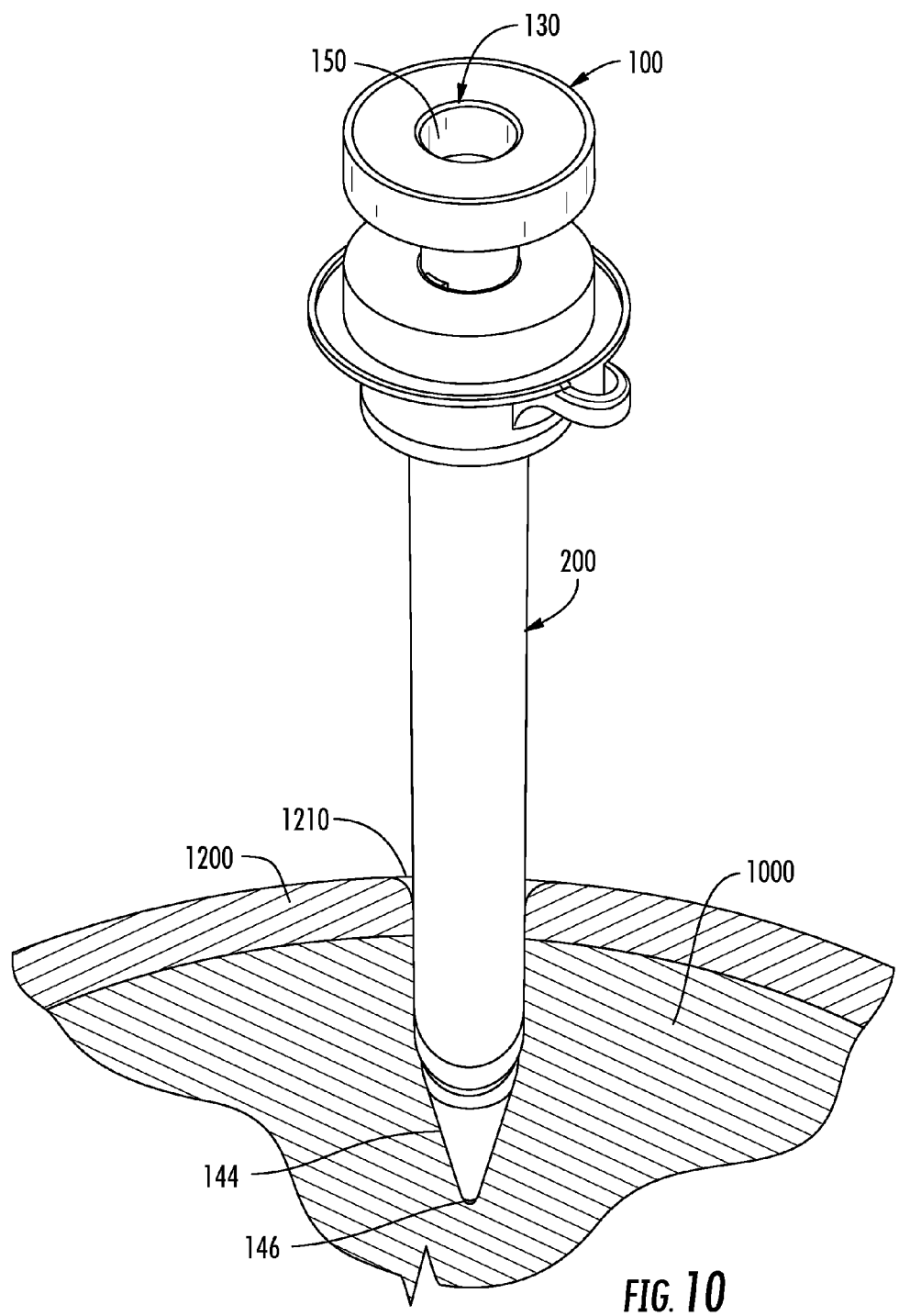
FIG. 10 is the perspective view shown in FIG. 9 with an obturator inserted into the lumen of the cannula.

With continued reference to FIG. 2, obturator 100 has a distal tip portion 144 beyond a distal end 116 of elongate tubular member 110. Distal tip portion 144 includes a distal tip 146. In embodiments, channel 150 extends from proximal end 130 of elongate tubular member 110 to distal tip 146 as shown in FIG. 3. Distal tip 146 permits the viewing of a body cavity 1000 through channel 150 as shown in FIG. 10 and as discussed in detail below. In some embodiments, distal dip 146 permits viewing through channel 150.

Figure 4:
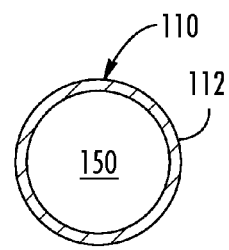
FIG. 4 is a top, cross-sectional view taken along the line 4-4 in FIG. 3.
Figure 5:
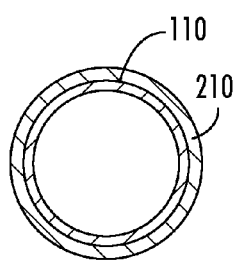
FIG. 5 is a top, cross-sectional view taken along the line 5-5 in FIG. 3.
Figure 6:
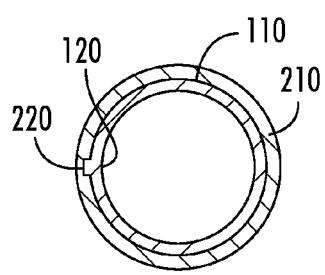
FIG. 6 is a top, cross-sectional view taken along the line 6-6 in FIG. 3.
Figure 7:
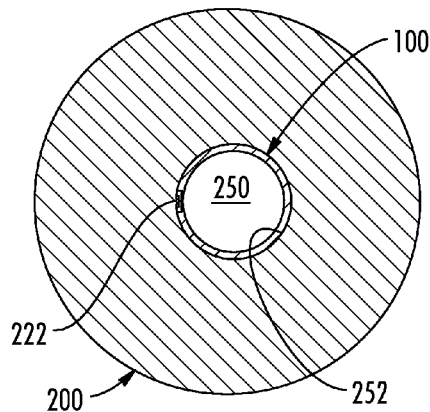
FIG. 7 is a top, cross-sectional view taken along the line 7-7 in FIG. 3.

Now referring to FIGS. 3 and 7, cannula 200 includes a tubular body member 210 having open proximal and distal ends 230, 240. A lumen 250 is defined between the proximal and distal ends 230, 240. Lumen 250 defines an inner surface 252 of tubular body member 210 and is sized to receive a portion of elongate tubular member 110 of obturator 100 as shown in FIGS. 4 and 5. Inner surface 252 includes a second mating structure 220 which receives first mating structure 120 when elongate tubular member 110 is received within lumen 250 as shown in FIG. 6.

Figure 3A:
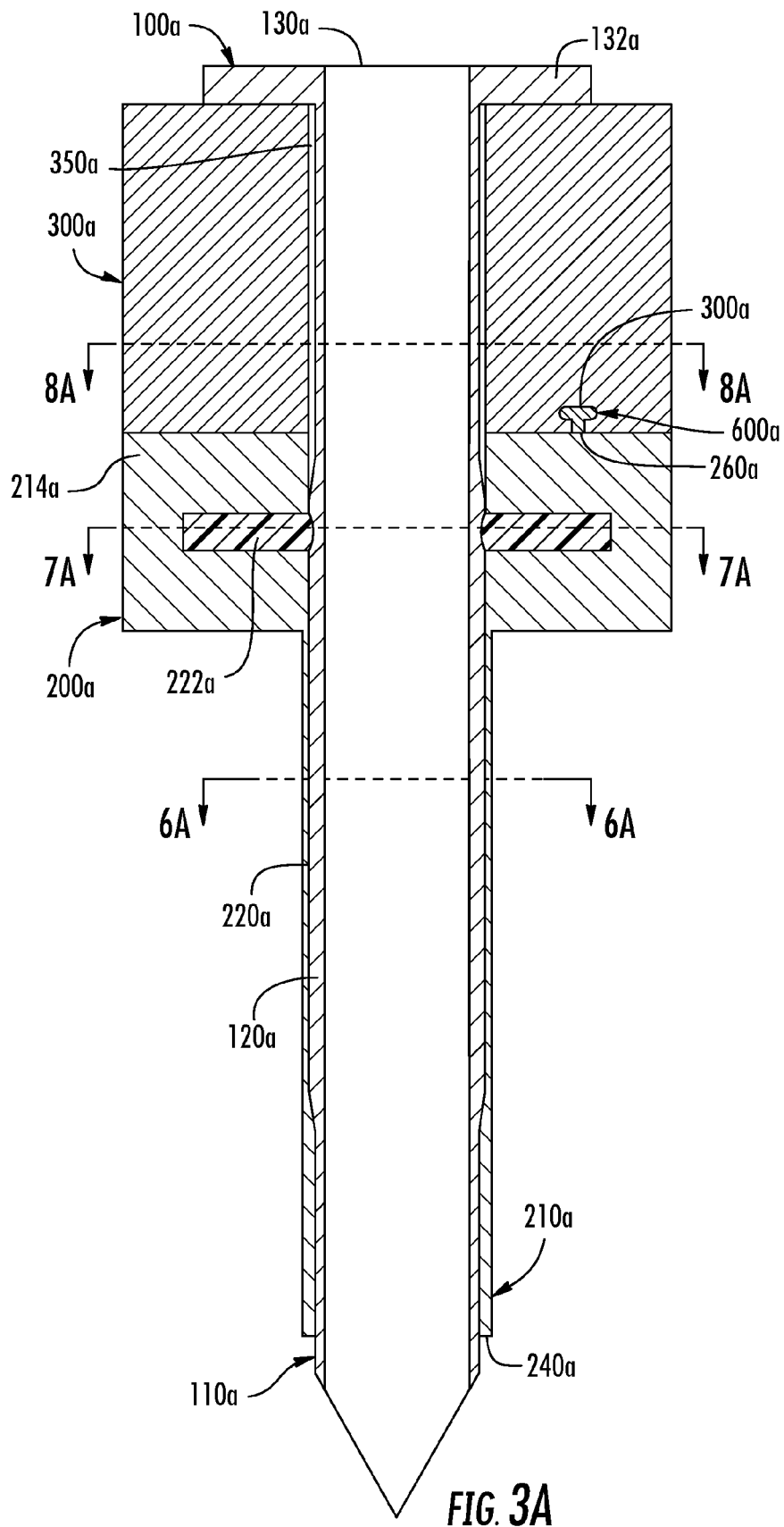
FIG. 3A is a side, cross-sectional view of a surgical assembly with an obturator having two first mating structures in accordance with the principles of the present disclosure.
Figure 3B:
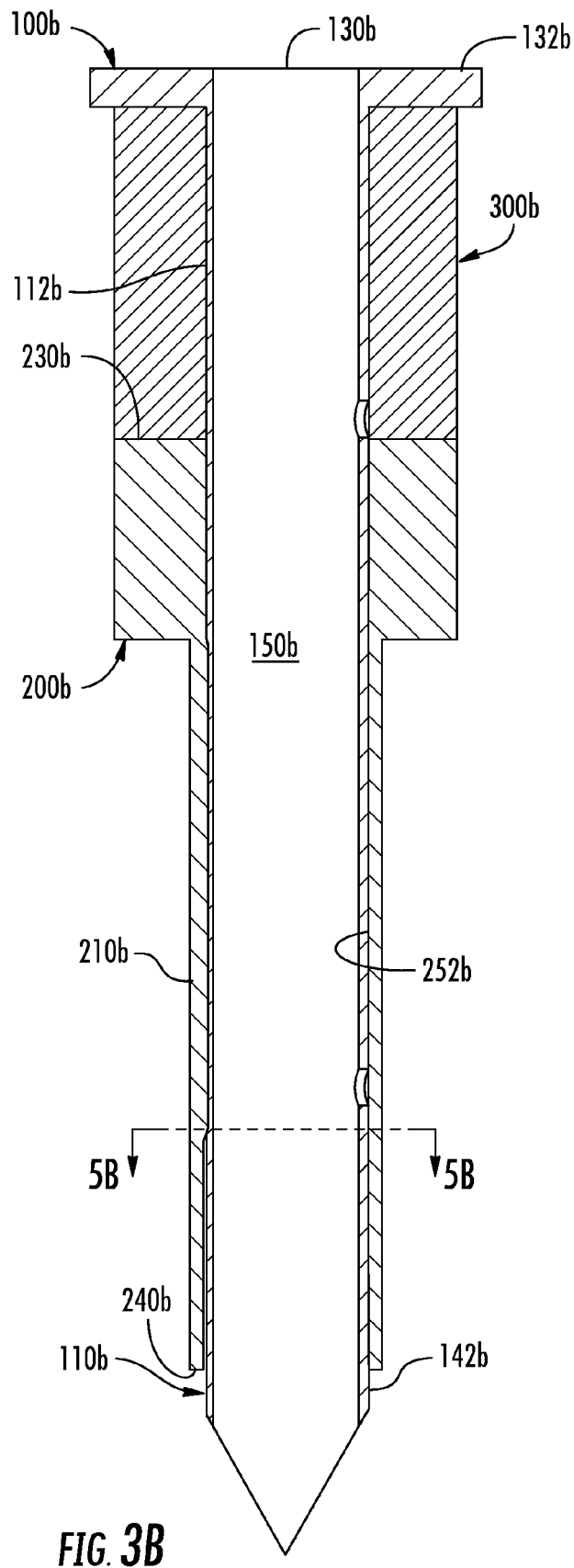
FIG. 3B is a side, cross-sectional view of a surgical assembly with an obturator having a first mating structure receiving a second mating structure in accordance with the principles of the present disclosure.
Figure 5B:
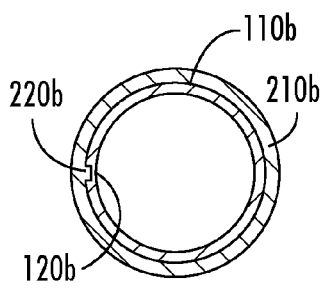
FIG. 5B is a top, cross-sectional view taken along the line 5B-5B in FIG. 3B.

As described above, second mating structure 220 of cannula 200 receives first mating structure 120 of obturator 100; however, as shown in FIGS. 3B and 5B, first mating structure 120b of obturator 100b may receive second mating structure 220b of cannula 200b. Either of the first mating structure or the second mating structure may be a protrusion, a wing, or an extended key member while the other mating structure may be an extended notch, a groove, or a slot configured to receive the other mating structure within.

Figure 6A:
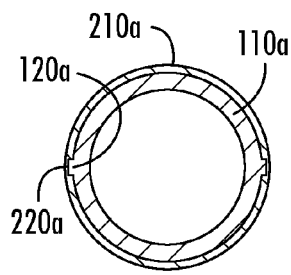
FIG. 6A is a top, cross-sectional view taken along the line 6A-6A in FIG. 3A.
Figure 6B:
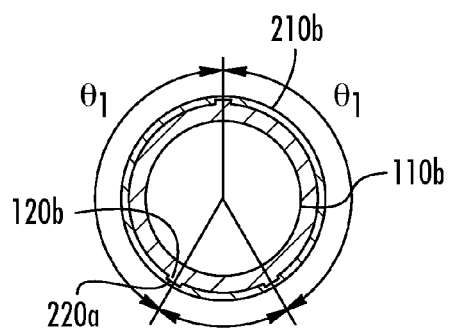
FIGS. 6B-6E are top, cross-sectional views illustrating surgical assemblies with other wing configurations in accordance with the principles of the present disclosure.
Figure 6C:
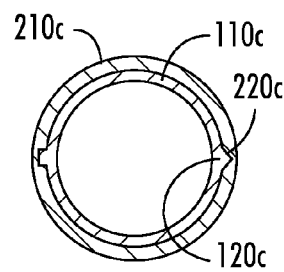
Figure 6D:
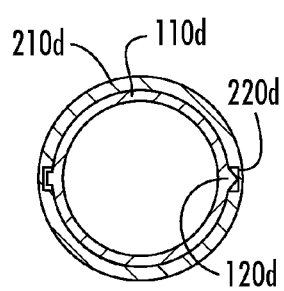
Figure 6E:
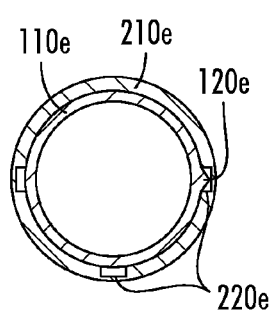

Referring now to FIGS. 6-6E, where first mating structure 120 is received within second mating structure 220, first mating structure 120 may have a plurality of shapes. Second mating structure 220 may be shaped to substantially conform to the shape of first mating structure 120 as shown in FIGS. 6-6C or second mating structure 220 may have a generic shape configured to accept a plurality of first mating structures 120 as shown in FIG. 6D. In embodiments, two or more first mating structures 120 are fixed to elongate tubular member 110 as illustrated in FIGS. 6A-6D. When obturator 100 has two or more first mating structures 120, cannula 200 includes two or more second mating structures 220. Each second mating structure 220 receiving a first mating structure 120. In some embodiments, when obturator 100 includes two or more first mating structures 120, each first mating structure 120 has the same shape as shown in FIG. 6A. In certain embodiments, when obturator 100 includes two or more first mating structures 120, at least one first mating structure 120 has a different shape than another first mating structure 120 as shown in FIGS. 6C and 6D. The shape of each second mating structure 220 may define one or more desired circumferential positions of the obturator 100 relative to the cannula 200 as shown in FIG. 6C. FIG. 6A is representative of embodiments where the two or more first mating structures 120 and the two or more second mating structures 220 are circumferentially spaced equally and FIG. 6B is representative of embodiments where the two or more first mating structures 120 and the two or more second mating structures 220 are circumferentially spaced unequally. In particular embodiments, the circumferential position of first mating structure 120 and second mating structure 220 define one or more desired circumferential positions of the obturator 100 relative to the cannula 200. It can be appreciated that inner surface 252 of tubular body member 210 may include more second mating structures 220 than obturator 100 has first mating structures 120 as shown in FIG. 6E. It will be appreciated that when second mating structure 220 is received within first mating structure 120, the structures above may be reversed, e.g., second mating structure 220 may be a wing on inner surface 252 and first mating structure 120 may be a slot in outer surface 112 that receives second mating structure 220.

Figure 7A:
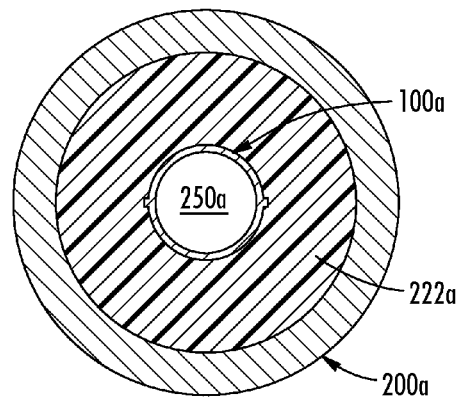
FIG. 7A is a top, cross-sectional view taken along the line 7A-7A in FIG. 3A.

According to aspects of the disclosure, cannula 200 includes a locking mechanism 222 as shown in FIGS. 7 and 7A. Locking mechanism 222 locks obturator 100 within lumen 250 of cannula 200. Locking mechanism 222 is at least one of a notch, a high friction surface, a detent, a rib, an elastomer member, an o-ring, or a tab. Locking mechanism 222 engages outer surface 112 of elongate tubular member 110 of obturator 100. In some embodiments, outer surface 112 includes a locking structure 122. In certain embodiments, locking structure 122 is disposed on first mating structure 120 (FIG. 2). Locking structure 122 is at least one of a notch, a high friction surface, a detent, a rib, an elastomer member, an o-ring, or a tab. For example, in FIGS. 3 and 7 locking mechanism 222 is a tab that engages locking structure 122 which is a detent. Alternatively, in FIGS. 3A and 7A, locking mechanism 222a is an elastomer material which engages locking structure 122a on first mating structure 120a which is a notch. In particular embodiments, locking mechanism 222a may engage the entire outer surface 112a of elongate tubular member 110a thereby forming a seal as shown in FIGS. 3A and 7A. It can be appreciated that this seal may obviate the need for a separate seal housing.

Now referring to FIG. 3A, an upper seal housing 300a includes a sealing port 350a. Sealing port 350a is coaxial with lumen 250a. Upper seal housing 300a may attach to a lower seal housing or proximal portion 214a of cannula 200a. In embodiments, upper seal housing 300a is attached to proximal portion 214a by a twisting or bayonet connection. In some embodiments, upper seal housing 300a and proximal portion 214a includes a securement mechanism 600a which secures upper seal housing 300a to cannula 200a. In certain embodiments, an upper housing portion 360a of securement mechanism 600a is disposed on upper seal housing 300a and a cannula portion 260a of securement mechanism 600a is disposed on proximal portion 214a of cannula 200a. Upper housing portion 360a and cannula portion 260a may cooperate to secure upper seal housing 300a and cannula 200a together. In particular embodiments, upper housing portion 360a and cannula portion 260a may cooperate to secure upper seal housing 300a and cannula 200a together in a fixed circumferential position relative to each other. Securement mechanism 600a may be at least one of a threaded connection or a bayonet-type connection with upper housing portion 360a and/or cannula portion 260a may be at least one of a detent, a tab, a groove, a rib, or other known means selectively securing upper seal housing 300a to cannula 200a.

Figure 8:
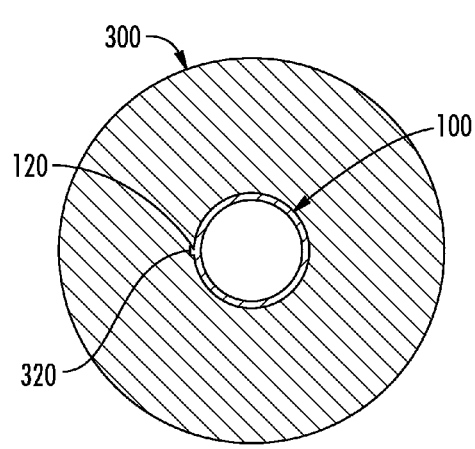
FIG. 8 is a top, cross-sectional view taken along the line 8-8 in FIG. 3.
Figure 8A:
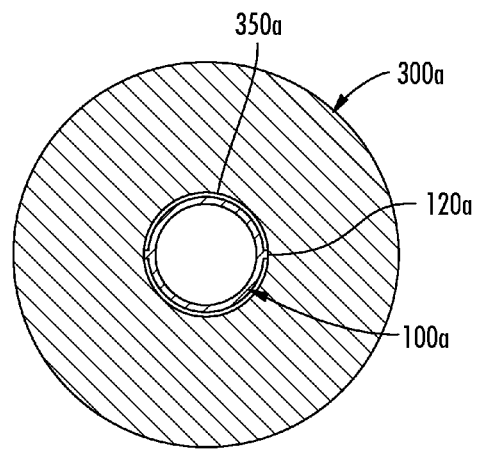
FIG. 8A is a top, cross-sectional view taken along the line 8A-8A in FIG. 3A.

Referring now to FIGS. 3 and 8, sealing port 350 is sized to permit a portion of elongate tubular member 110 of obturator 100 pass through when obturator 100 is received within lumen 250 of cannula 200. When obturator 100 is received within cannula 200, a sealing member 352 forms a seal with outside surface 112 of elongate tubular member 110. In embodiments, sealing port 350a is sized to permit first mating structure 120a to pass through in any circumferential position as shown in FIG. 8A. Referring back to FIGS. 3 and 8, sealing port 350 includes a third mating structure 320. Third mating structure 320 may align with second mating structure 220 when upper seal housing 300 is secured to cannula 200. The alignment of third mating structure 320 with second mating structure 220 may define the fixed circumferential position. In certain embodiments, sealing port 350 is sized to only permit elongate tubular member 110 of obturator 100 to pass through when first mating structure 120 is aligned with third mating structure 320. When obturator 100 is received within lumen 250 of cannula 200, first mating structure 120 may be fully disposed within cannula 200 as shown in FIG. 3A or first mating structure 120 may extend into sealing housing 300 as shown in FIG. 3. It will be appreciated that when assembly 10 includes two or more first mating structures 120 and two or more second mating structures 220, sealing port 350 may include two or more third mating structures 320. Each third mating structure 320 may align with a second mating structure 220 and receive a first mating structure 120 or permit a first mating structure 120 to pass. It will also be appreciated that each third mating structure 320 may also be shaped similar to each second mating structure 220 as described above. It will be further appreciated that when second mating structure 220 is received within first mating structure 120, third mating structure 320 may also be received within first mating structure 120.

Referring now to FIG. 3A, first mating structure 120a engages second mating structure 220a when obturator 100a is rotated. Obturator 100a rotates when an external rotational force, clocking force, or torque is applied to a proximal portion 132a of obturator 100a. The cooperation of first and second mating structures 120a, 220a maintain obturator 100a and cannula 200a in a fixed circumferential position relative to each other as described in detail below. Proximal portion 132a may also prevent obturator 100a from fully passing through lumen 250a of cannula 200a.

When a torque is applied to proximal portion 132a while elongate tubular member 110a of obturator 100a is disposed within lumen 250a of cannula 200a, first mating structure 120a engages second mating structure 220a transferring at least a portion of the torque to cannula 200a, cannula 200a thereby cooperates with the rotation of obturator 100a. In some embodiments, securement mechanism 600a maintains cannula 200a in a fixed circumferential position relative to upper seal housing 300a when cannula 200a is rotated by obturator 100a. In certain embodiments, cannula portion 260a of securement mechanism 600a engages upper housing portion 360a of securement mechanism 600a when cannula 200a rotates transferring at least a portion of the torque to upper seal housing 300a such that upper seal housing 300a cooperates with the rotation of cannula 200a. It can be appreciated that the torque may be applied directly to cannula 200a with a portion of the torque being transferred to obturator 100a second mating structure 220a engaging first mating structure 120a.

Now referring to FIG. 3, first mating structure 120 may engage second mating structure 220 of cannula 200 and third mating structure 320 of upper seal housing 300 when a torque is applied to proximal portion 132 transferring at least a portion of the torque to cannula 200 and at least a portion of the torque to upper seal housing 300 such that cannula 200 and upper seal housing 300 both cooperate with the rotation of obturator 100 maintaining a fixed circumferential position relative to obturator 100.

According to aspects of the present disclosure, a method for viewing a cavity is disclosed. The method includes the steps of accessing an opening with a cannula, inserting an obturator into a lumen of the cannula, and viewing a cavity through the obturator. The step of inserting the obturator may include locking an obturator within the lumen of the cannula. In some embodiments, the method includes the step of rotating the obturator to a desired viewing position after the step of inserting the obturator. In certain embodiments, the method includes the step of securing a seal housing to the cannula before the step of inserting the obturator. The step of securing the seal housing may further include aligning a mating structure disposed within a sealing port of the seal housing with a mating structure within an inner surface of a tubular body member of the cannula. The method may include any of the features of assembly 10 discussed above, namely obturator 100, cannula 200, and upper seal housing 300.

Figure 9:
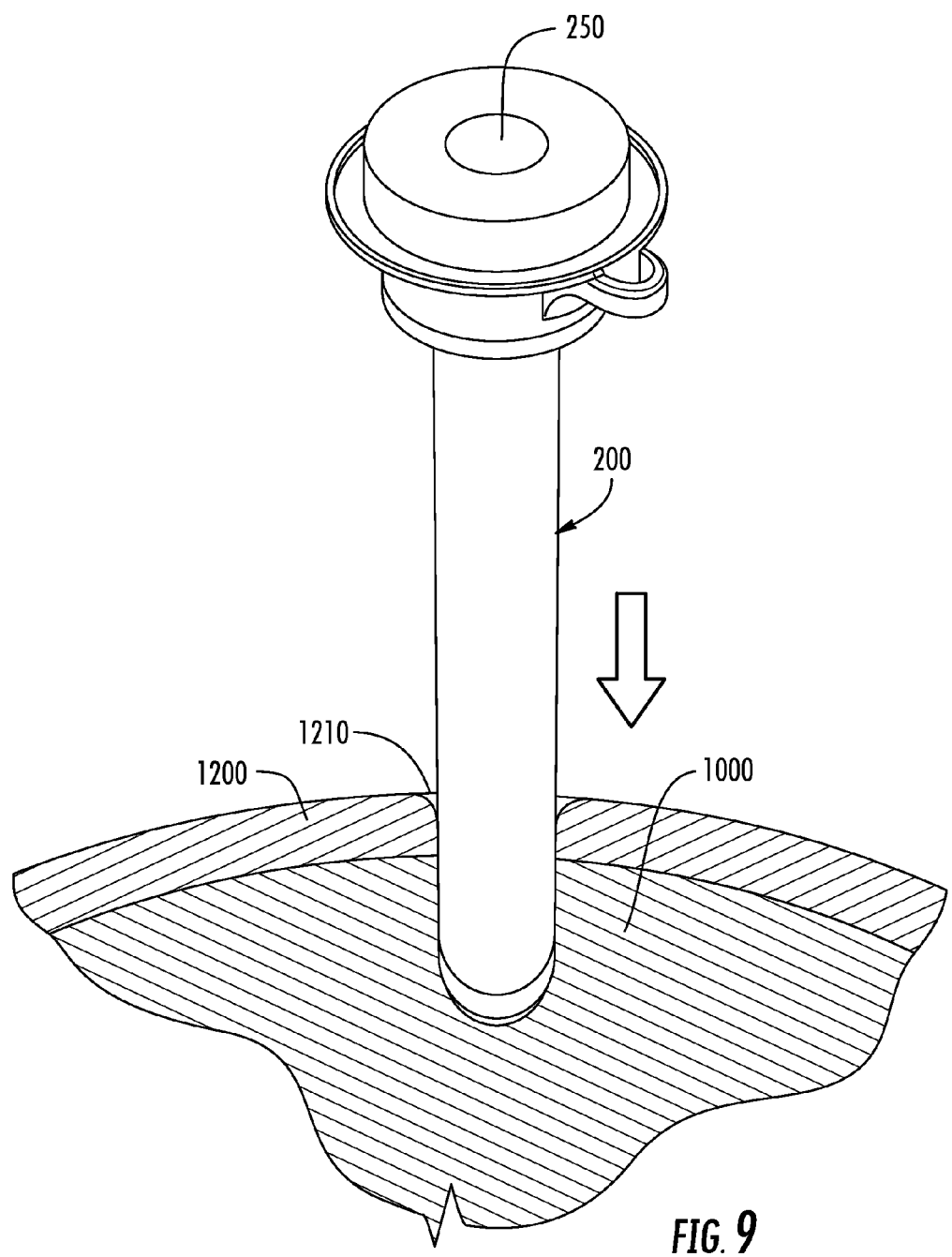
FIG. 9 is a perspective view of a cannula accessing a body cavity in accordance with the principles of the present disclosure.
Figure 11:
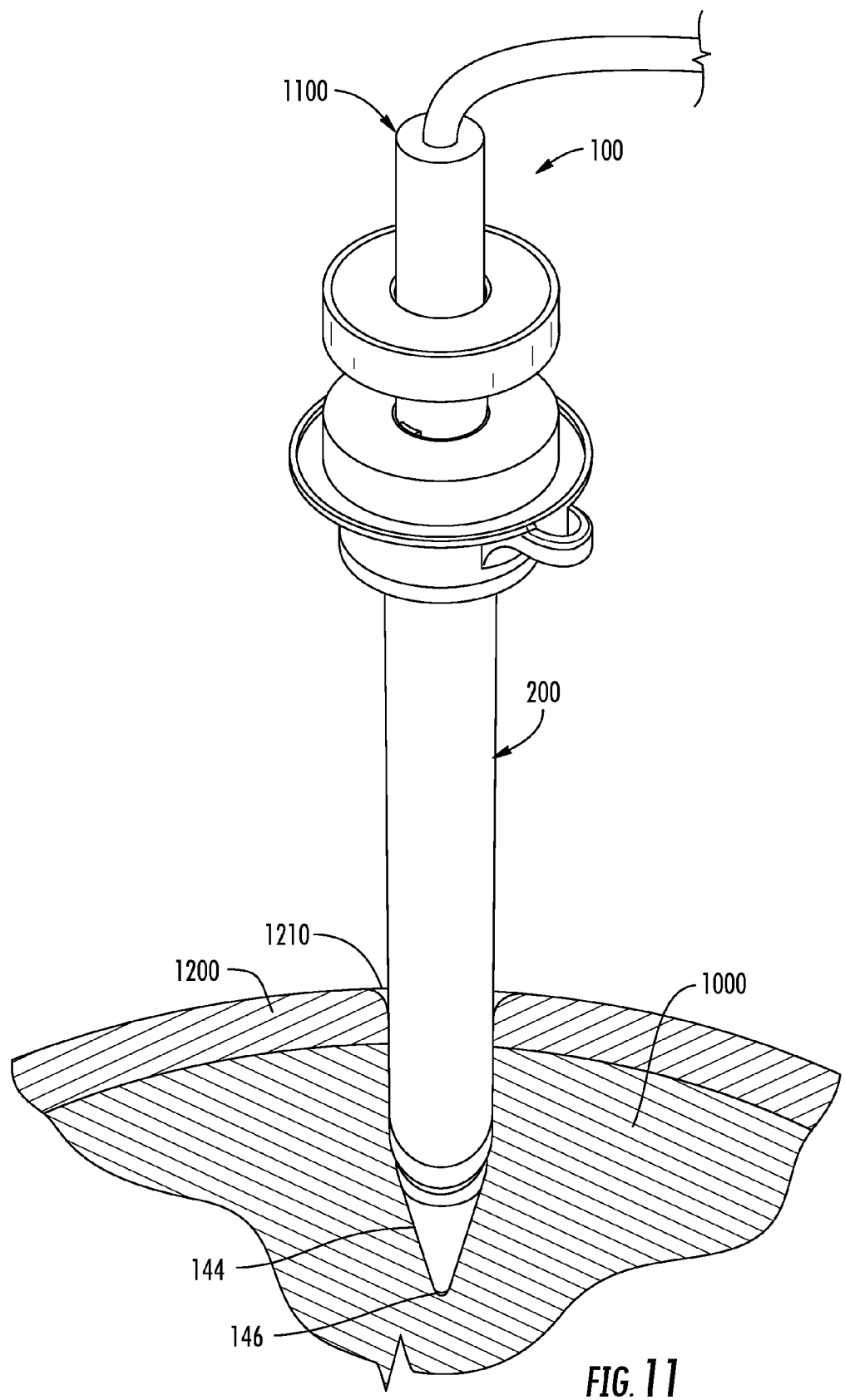
FIG. 11 is the perspective view shown in FIG. 10 with an instrument inserted within the channel of the obturator.

The method may be used to view a body cavity 1000 as shown in FIGS. 9-11. First, a clinician accesses an opening 1210 in a tissue layer 1200. Opening 1210 provides access to an underlying body cavity 1000 and may be a naturally occurring orifice, an incision created by the clinician, or a wound. The clinician accesses opening 1210 by placing a cannula 200 having a lumen 250 within opening 1210 as shown in FIG. 9. Then, the clinician inserts an obturator 100 into lumen 250 of cannula 200 as shown in FIG. 10. Obturator 100 may include a channel 150 extending from an open proximal end 130 to a distal tip portion 144 of obturator 100. Channel 150 may permit direct viewing of body cavity 1000 through distal tip 146. Channel 150 may also receive an instrument 1100 which allows a clinician to view body cavity 1000 through distal tip 146 as shown in FIG. 11. Instrument 1100 may be an optical scope (not shown) to allow direct viewing of body cavity 1000 through an eyepiece (not shown). Alternatively, instrument 1100 may include an optical assembly (not shown) that views body cavity 1000 through distal tip 146 and captures an image. The captured image is displayed on a monitor (not shown) allowing a clinician to view body cavity 1000. In certain embodiments, instrument 1100 magnifies at least a portion of body cavity 1000.

One advantage of an obturator with features for mating with a cannula is that a rotatably connectable upper seal housing is prevented from inadvertently rotating relative to a lower seal housing or cannula during use. Such inadvertent rotation of the upper seal housing relative to the cannula may be particularly important in embodiments in which the obturator is bladeless, since it is often the case that bladeless obturators are "clocked" (inserted using a back-and-forth twisting motion while simultaneously providing a distal force) in order to facilitate entry through tissue layers and into the body. This clocking motion may increase the likelihood for inadvertent rotation, and thus inadvertent disconnection, of the upper seal housing relative to the cannula. Of course, these twisting forces may also occur when a bladed, e.g., sharp, obturator assembly is employed, and thus the present disclosure, in accordance with various embodiments thereof, is also applicable to embodiments that employ a bladed obturator assembly. By maintaining the obturator, the cannula, and the seal housing in a fixed circumferential position relative to one another it may be less likely that the seal housing will separate from the cannula and maintain a seal between the cannula and the obturator. This seal may maintain a sterile environment within an underlying body cavity. The seal may also maintain an insufflation pressure within the underlying body cavity.

Another advantage of an obturator with features for mating with a cannula is that a reduction in the amount of rotation needed to connect an upper seal housing to the cannula may be achieved. Various existing rotatable valve housing connection arrangements (e.g., existing valve housing connection arrangements that employ a bayonet type connection between the upper seal housing and the cannula, typically requires that the upper seal housing be rotated a quarter turn, e.g., 90 degrees, relative to the cannula. By providing mating structures, such as the first mating structure 120a and the second mating structure 220a shown in the example embodiments of FIG. 3a, the amount of rotation needed for connecting the upper seal housing and the cannula may be reduced so as to be smaller than a quarter turn. This reduction in the amount of rotation needed in order to connect the upper seal housing and the cannula may make it easier for a user, e.g., a surgeon, to remove the upper seal housing from the cannula during surgery, especially if the surgeon desires to, or is only able to, use a single hand to do so, as is often the case in complicated surgical procedures.

It will be understood that various modifications may be made to the embodiments and aspects disclosed herein. Therefore, the above description should not be construed as limiting, but merely as exemplifications of preferred embodiments. Those skilled in the art will envision other modifications within the scope and spirit of the claims appended hereto.

What is claimed:

1. A surgical assembly, comprising:
   an obturator including an elongate tubular member having an outer surface, a first mating structure, and a proximal end, the first mating structure fixed to the outer surface;
   a cannula including a tubular body member having open proximal and distal ends defining a lumen therebetween, the lumen defining an inner surface of the tubular body member, the lumen configured to receive the elongate tubular member of the obturator, the inner surface having a second mating structure which receives the first mating structure when the lumen receives the elongate tubular member, the first mating structure engaging the second mating structure to rotate the cannula when the obturator is rotated; and
   an upper seal housing attached to a proximal portion of the cannula, the upper seal housing having a sealing port disposed over the lumen, a portion of the elongate tubular member of the obturator passes through the sealing port, the sealing port forming a seal with the outer surface of the elongate tubular member, the upper seal housing including a third mating structure aligned with the second mating structure of the tubular body member of the cannula when the upper seal housing is attached to the proximal portion of the cannula, the third mating structure receiving a portion of the first mating structure when the elongate tubular member of the obturator is received within the lumen of the cannula.

2. The surgical assembly of claim 1, wherein the obturator includes a distal tip portion beyond a distal end of the elongate tubular member, the distal tip portion permitting viewing of a body cavity.

3. The surgical assembly of claim 1, wherein the tubular body member of the cannula includes a locking mechanism, the locking mechanism engages the first mating structure to lock the obturator within the lumen.

4. The surgical assembly of claim 3, wherein the locking mechanism is at least one of a high friction surface, a detent, a rib, an elastomer member, an o-ring, or a tab.

5. The surgical assembly of claim 3, wherein the first mating structure includes a notch and the locking mechanism engages the notch.

6. The surgical assembly of claim 1, wherein the first mating structure is disposed entirely within the second mating structure of the tubular body member of the cannula when the elongate tubular member of the obturator is received within the lumen of the cannula.

7. The surgical assembly of claim 1, wherein the obturator includes two or more first mating structures fixed to the outer surface of the elongate tubular member and the cannula includes two or more second mating structures of the tubular body member, each first mating structure received within a respective second mating structure.

8. The surgical assembly of claim 7, wherein the two or more first mating structures are circumferentially spaced equally on the outer surface of the elongate tubular member of the obturator.

9. The surgical assembly of claim 7, wherein the two or more first mating structures are circumferentially spaced unequally on the outer surface of the elongate tubular member of the obturator, unequal circumferential spacing defines a desired circumferential position of the obturator relative to the cannula.

10. The surgical assembly of claim 1, wherein the cooperation of the first mating structure and the second mating structure defines a desired circumferential position of the obturator relative to the cannula.

* * * * *